US00PP21637P2

(12) United States Plant Patent
Westhoff

(10) Patent No.: US PP21,637 P2
(45) Date of Patent: Jan. 18, 2011

(54) ***VERBENA* PLANT NAMED 'WESVEREME'**
(50) Latin Name: *Verbena tenera*
Varietal Denomination: Wesvereme

(75) Inventor: Heinrich Westhoff, Südlohn (DE)

(73) Assignee: Gartenbau und Spezialkulteren Westhoff GbR, Südlohn (DE)

( * ) Notice: Subject to any disclaimer, the term of this patent is extended or adjusted under 35 U.S.C. 154(b) by 0 days.

(21) Appl. No.: 12/587,420

(22) Filed: Oct. 7, 2009

(51) Int. Cl.
*A01H 5/00* (2006.01)

(52) U.S. Cl. ..... Plt./308
(58) Field of Classification Search ..... Plt./308
See application file for complete search history.

*Primary Examiner*—June Hwu
(74) *Attorney, Agent, or Firm*—C. A. Whealy

(57) ABSTRACT

A new and distinct cultivar of *Verbena* plant named 'Wesvereme', characterized by its compact and mounding plant habit; vigorous growth habit; medium-sized leaves; freely flowering habit; and dark red purple-colored flowers that are held above and beyond the foliar plane in rounded umbels.

1 Drawing Sheet

Botanical designation: *Verbena tenera.*
Cultivar denomination: 'WESVEREME'.

CROSS-REFERENCED TO RELATED APPLICATIONS

Title: *Verbena* Plant Named 'Wesverepea'.
Applicant: Heinrich Westhoff.
Filed: Concurrently with this application (U.S. Plant patent application No. 12/587,484).
Title: *Verbena* Plant Named 'Wesverevoo'.
Applicant: Heinrich Westhoff.
Filed: Concurrently with this application (U.S. Plant patent application No. 12/587,421).

BACKGROUND OF THE INVENTION

The present invention relates to a new and distinct cultivar of *Verbena* plant, botanically known as *Verbena tenera,* and hereinafter referred to by the name 'Wesvereme'.

The new *Verbena* plant is a product of a planned breeding program conducted by the Inventor in Südlohn, Germany. The objective of the breeding program is to create new compact *Verbena* plants with numerous attractive flowers.

The new *Verbena* plant originated from a cross-pollination made by the Inventor in April, 2004 in Südlohn, Germany of a proprietary seedling selection of *Verbena tenera* identified as code number 04P104, not patented, as the female, or seed, parent with a proprietary seedling selection of *Verbena tenera* identified as code number 04P212, not patented, as the male, or pollen, parent. The new *Verbena* plant was discovered and selected by the Inventor as a single flowering plant within the progeny of the stated cross-pollination in a controlled environment in Südlohn, Germany in August, 2005.

Asexual reproduction of the new *Verbena* plant by terminal cuttings in a controlled environment in Südlohn, Germany since 2005 has shown that the unique features of this new *Verbena* plant are stable and reproduced true to type in successive generations.

SUMMARY OF THE INVENTION

Plants of the new *Verbena* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Wesvereme'. These characteristics in combination distinguish 'Wesvereme' as a new and distinct cultivar of *Verbena:*

1. Compact and mounding plant habit.
2. Vigorous growth habit.
3. Medium-sized leaves.
4. Freely flowering habit.
5. Dark red purple-colored flowers that are held above and beyond the foliar plane in rounded umbels.

Plants of the new *Verbena* can be compared to plants of the female parent selection. Plants of the new *Verbena* differ primarily from plants of the female parent selection in the following characteristics:

1. Plants of the new *Verbena* have smaller leaves than plants of the female parent selection.
2. Plants of the new *Verbena* have larger flowers than plants of the female parent selection.
3 Plants of the new *Verbena* and the female parent selection differ in flower color as plants of the female parent selection have peach-colored flowers.

Plants of the new *Verbena* can be compared to plants of the male parent selection. Plants of the new *Verbena* differ primarily from plants of the male parent selection in the following characteristics:

1. Plants of the new *Verbena* are more compact and mounding than plants of the male parent selection.
2. Plants of the new *Verbena* have denser inflorescences with more flowers per inflorescence than plants of the male parent selection.
3. Plants of the new *Verbena* and the male parent selection differ in flower color as plants of the male parent selection have plum-colored flowers.

Plants of the new *Verbena* differ primarily from plants of the *Verbenas* 'Wesverepea' and 'Wesverevoo' in flower color as plants of 'Wesverepea' have peach-colored flowers and plants of 'Wesverevoo' have red-colored flowers.

Plants of the new *Verbena* can be compared to plants of the *Verbena* 'Wesverscar', disclosed in U.S. Plant Pat. No.

15,988. In side-by-side comparisons conducted in Südlohn, Germany, plants of the new *Verbena* differed primarily from plants of 'Wesverscar' in the following characteristics:

1. Plants of the new *Verbena* were more compact and mounding than plants of 'Wesverscar'.
2. Plants of the new *Verbena* were more freely branching than plants of 'Wesverscar'.
3. Plants of the new *Verbena* had shorter internodes than plants of 'Wesverscar'.
4. Plants of the new *Verbena* and 'Wesverscar' differed in flower color as plants of 'Wesverscar' had dark red-colored flowers.

Plants of the new *Verbena* can be compared to plants of the *Verbena* 'Wesverdark', disclosed in U.S. Plant Pat. No. 13,847. In side-by-side comparisons conducted in Südlohn, Germany, plants of the new *Verbena* differed primarily from plants of 'Wesverdark' in the following characteristics:

1. Plants of the new *Verbena* were more compact and mounding than plants of 'Wesverdark'.
2. Plants of the new *Verbena* had shorter internodes than plants of 'Wesverdark'.
3. Plants of the new *Verbena* had smaller leaves than plants of 'Wesverdark'.
4. Plants of the new *Verbena* and 'Wesverdark' differed in flower color as plants of 'Wesverdark' had red-colored flowers.

BRIEF DESCRIPTION OF THE PHOTOGRAPH

The accompanying colored photograph illustrates the overall appearance of the new *Verbena* plant, showing the colors as true as it is reasonably possible to obtain in colored reproductions of this type. Colors in the photograph may differ slightly from the color values cited in the detailed botanical description which accurately describe the colors of the new *Verbena* plant. The photograph comprises a side perspective view of a typical flowering plant of 'Wesvereme' grown in a container.

DETAILED BOTANICAL DESCRIPTION

The aforementioned photograph and following observations, measurements and values describe plants grown in Südlohn, Germany in a glass-covered greenhouse during the summer and under conditions which closely approximate commercial production. During the production of the plants, day temperatures ranged from 20° C. to 25° C., night temperatures ranged from 16° C. to 18° C. and light levels ranged from 3,000 to 50,000 lux. Plants were 30 weeks old when the photograph and the description were taken. In the description, color references are made to The Royal Horticultural Society Colour Chart, 2001 Edition, except where general terms of ordinary dictionary significance are used.

Botanical classification: *Verbena tenera 'Wesvereme'*.

Parentage:

*Female, or seed, parent.*—Proprietary seedling selection of *Verbena tenera* identified as code number 04P104, not patented.

*Male, or pollen, parent.*—Proprietary seedling selection of *Verbena tenera* identified as code number 04P212, not patented.

Propagation:

*Type.*—Terminal cuttings.

*Time to initiate roots.*—About 14 to 18 days at 18° C.

*Time to produce a rooted cutting.*—About 21 to 26 days at 18° C.

*Root description.*—Fibrous, medium in thickness; color, close to 158A.

*Rooting habit.*—Freely branching; moderately dense to dense.

Plant description:

*Plant habit.*—Initially upright, then compact and mounding growth habit; freely branching habit with two lateral branches potentially forming at every node; pinching enhances lateral branch development; dense and bushy plant habit; vigorous growth habit.

*Plant height.*—About 23 cm to 28 cm.

*Plant diameter.*—About 58 cm to 60 cm.

Lateral branch description:

*Length.*—About 25 cm to 50 cm.

*Diameter.*—About 1.9 mm to 2.3 mm.

*Internode length.*—About 1.5 cm.

*Texture.*—Densely pubescent; viscid.

*Color.*—Close to 144A.

Foliage description:

*Arrangement.*—Opposite, simple; sessile.

*Length.*—About 4.3 cm.

*Width.*—About 2.3 cm.

*Shape.*—Ovate to deltoid.

*Apex.*—Acute.

*Base.*—Attenuate.

*Margin.*—Dentate to crenate.

*Texture, upper and lower surfaces.*—Densely pubescent, viscid.

*Venation pattern.*—Pinnate.

*Color.*—Developing and fully expanded leaves, upper surface: Close to 147A; venation, close to 147B. Developing and fully expanded leaves, lower surface: Close to 147B; venation, close to 147C.

Flower description:

*Flower arrangement and habit.*—Salverform flowers arranged in hemispherical terminal umbels; umbels dense and mounding; numerous umbels covering the entire plant; flowers face upward or outward; freely flowering habit with about 15 to 33 flowers per inflorescence.

*Natural flowering season.*—Plants flower continuously from April until frost in the fall in Germany; plants begin flowering about 12 to 14 weeks after planting.

*Flower longevity.*—Flowers last about two weeks on the plant; flowers persistent.

*Fragrance.*—None detected.

*Inflorescence size.*—Diameter: About 6.3 cm. Height: About 3.4 cm.

*Flowers.*—Appearance: Flared trumpet, corolla fused, five-parted; sessile. Length: About 3.3 cm. Diameter: About 2.3 cm. Tube length: About 2.2 cm. Throat diameter: About 2.4 mm. Tube diameter, base: About 1.9 mm.

*Flower buds.*—Length: About 1.9 cm. Diameter: About 6 mm. Shape: Oblong. Color: Towards the apex, close to 71A; mid-section and base, close to 145C.

*Corolla.*—Arrangement: Single whorl of five fused petals. Petal lobe length: About 1.15 cm. Petal lobe width: About 1 cm. Petal lobe shape: Broadly ovate to cordate. Petal lobe apex: Emarginate. Petal margin: Entire. Petal texture, upper and lower surfaces: Smooth, glabrous; velvety. Color: Petal, when opening, upper surface: Close to 60A. Petal, when opening, lower surface: Close to 60C. Petal, fully opened, upper surface: Close to 61A to 61B. Petal, fully opened, lower surface: Close to 72A to 72C; color becoming closer to N74C with development. Throat: Close to 145D. Tube: Close to 145C.

*Calyx.*—Arrangement: Star-shaped calyx with five fused sepals. Sepal length: About 1.3 cm. Sepal width: About 2.9 mm. Sepal shape: Lanceolate. Sepal apex: Acute. Sepal margin: Entire. Sepal texture, upper and lower surfaces: Pubescent, viscid; velvety. Sepal color, upper and lower surfaces: Close to 146A.

*Peduncles.*—Length: About 2.1 cm to 6.2 cm. Diameter: About 1.3 mm. Strength: Strong; wiry. Texture: Pubescent, viscid. Color: Close to 146A.

*Reproductive organs.*—Stamens: Quantity/arrangement: Four per flower, adnate to corolla tube. Anther shape: Two-parted; ovate. Anther length: About 1.5 mm. Anther diameter: About 1.3 mm. Anther color: Close to 154A. Pollen amount: Scarce. Pollen color: Close to 1A. Pistils: Quantity: One per flower. Pistil length: About 1.9 cm. Stigma shape: Ovate. Stigma color, immature: Close to 146C. Stigma color, mature: Close to 146A. Style length: About 1.3 cm. Style color: Close to 145C. Ovary color: Close to 145A. Seeds: Length: About 5 mm. Diameter: About 1.1 mm. Color: Close to 197A.

Temperature tolerance: Plants of the new *Verbena* have been observed to tolerate temperatures from about 5° C. to about 30° C.

Pathogen/pest resistance: Plants of the new *Verbena* have not been observed to be resistant to pathogens and pests common to *Verbenas*.

It is claimed:

1. A new and distinct *Verbena* plant named 'Wesvereme' as illustrated and described.

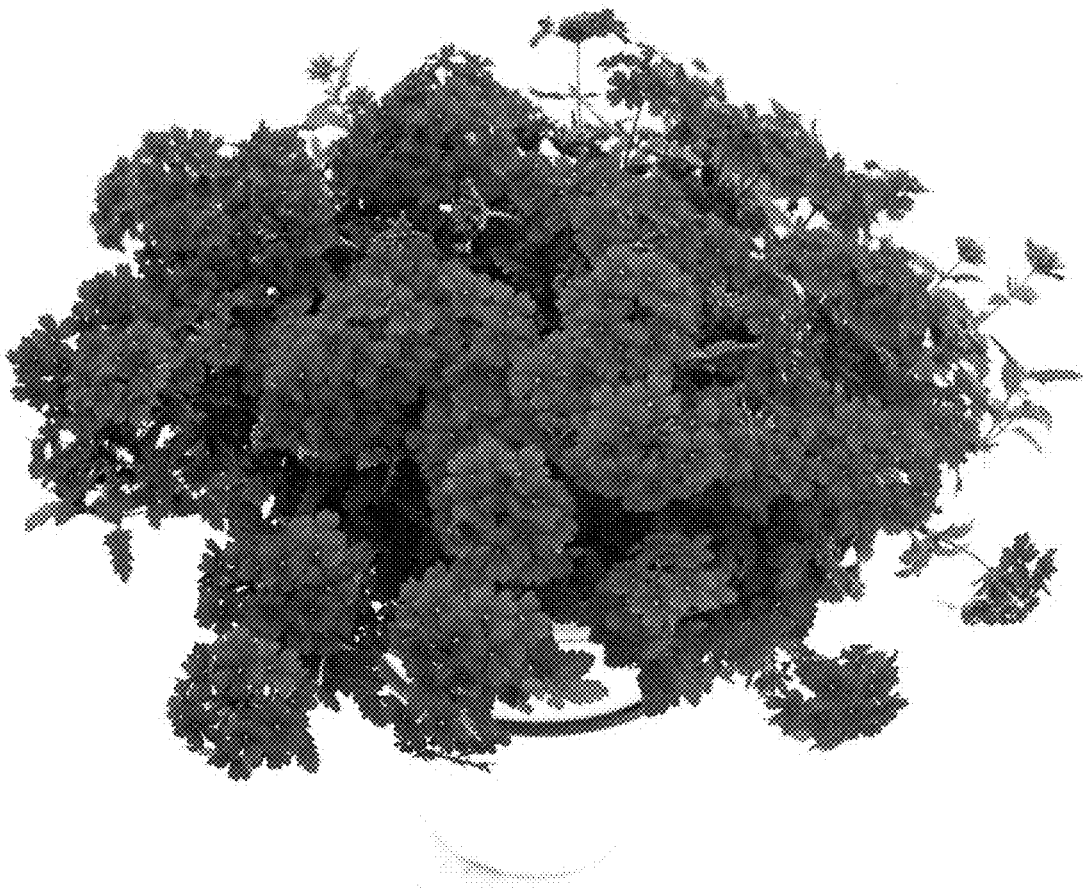

* * * * *